US010383631B2

(12) United States Patent
Collings et al.

(10) Patent No.: US 10,383,631 B2
(45) Date of Patent: Aug. 20, 2019

(54) VARIABLE SPEED CONTROL OF POWERED SURGICAL DEVICE

(71) Applicant: Covidien LP, Mansfield, MA (US)

(72) Inventors: Peter Collings, Shelton, CT (US); Japhet Colon, New Haven, CT (US)

(73) Assignee: Covidien LP, Mansfield, MA (US)

( * ) Notice: Subject to any disclaimer, the term of this patent is extended or adjusted under 35 U.S.C. 154(b) by 451 days.

(21) Appl. No.: 15/228,219

(22) Filed: Aug. 4, 2016

(65) Prior Publication Data

US 2018/0036004 A1 Feb. 8, 2018

(51) Int. Cl.
*A61B 17/072* (2006.01)
*A61B 17/00* (2006.01)

(52) U.S. Cl.
CPC ................... *A61B 17/07207* (2013.01); *A61B 2017/00017* (2013.01); *A61B 2017/00039* (2013.01); *A61B 2017/00057* (2013.01); *A61B 2017/00367* (2013.01); *A61B 2017/00398* (2013.01); *A61B 2017/07257* (2013.01); *A61B 2017/07271* (2013.01); *A61B 2017/07285* (2013.01)

(58) Field of Classification Search
CPC ........... A61B 2017/00057; A61B 2017/00039; A61B 2017/00017
USPC ............................ 227/175.1–182.1; 250/221
See application file for complete search history.

(56) References Cited

U.S. PATENT DOCUMENTS

| | | | |
|---|---|---|---|
| 4,164,711 A | 8/1979 | Steckler et al. | |
| 4,600,867 A | 7/1986 | Hayashi et al. | |
| 4,705,038 A | 11/1987 | Sjostrom et al. | |
| 5,712,543 A | 1/1998 | Sjostrom | |
| 5,804,936 A | 9/1998 | Brodsky et al. | |
| 6,037,724 A | 3/2000 | Buss et al. | |
| 7,422,139 B2 | 9/2008 | Shelton, IV et al. | |
| 7,479,608 B2 | 1/2009 | Smith | |
| 7,481,347 B2 | 1/2009 | Roy | |
| 7,959,050 B2 | 6/2011 | Smith et al. | |
| 8,573,465 B2 | 11/2013 | Shelton, IV | |
| 8,968,276 B2 | 3/2015 | Zemlok et al. | |
| 9,053,877 B2 * | 6/2015 | Young | H01H 13/14 |
| 9,055,943 B2 | 6/2015 | Zemlok et al. | |
| 2006/0047271 A1 | 3/2006 | McPherson et al. | |
| 2007/0027469 A1 | 2/2007 | Smith et al. | |

(Continued)

FOREIGN PATENT DOCUMENTS

| | | |
|---|---|---|
| EP | 394216 A2 | 10/1990 |
| EP | 2923647 A2 | 9/2015 |
| EP | 3047806 A1 | 7/2016 |

OTHER PUBLICATIONS

U.S. Appl. No. 62/291,775, filed Feb. 5, 2016.
European Search Report dated Dec. 18, 2917, issued in EP 17184656.

*Primary Examiner* — Robert F Long
*Assistant Examiner* — Xavier A Madison

(57) ABSTRACT

A surgical device includes a housing, a drive shaft, a motor, a control button, and a motor speed controller. The motor is configured to rotate the drive shaft that is disposed within housing. The control button is disposed on the housing and the motor speed controller is operably associated with the control button. The motor speed controller varies an angular velocity of the motor as a function of a percent of actuation of the control button between an unactuated position and a fully actuated position.

12 Claims, 7 Drawing Sheets

(56) References Cited

U.S. PATENT DOCUMENTS

| | | | | |
|---|---|---|---|---|
| 2007/0147806 | A1* | 6/2007 | Schneider | A61B 17/1626 388/827 |
| 2007/0270884 | A1 | 11/2007 | Smith et al. | |
| 2008/0029376 | A1* | 2/2008 | Ngoagouni | H01H 13/20 200/345 |
| 2009/0209990 | A1 | 8/2009 | Yates et al. | |
| 2009/0240272 | A1 | 9/2009 | Shadeck et al. | |
| 2011/0204119 | A1 | 8/2011 | McCuen | |
| 2011/0210156 | A1 | 9/2011 | Smith et al. | |
| 2012/0089131 | A1* | 4/2012 | Zemlok | A61B 17/07207 606/1 |
| 2012/0199633 | A1 | 8/2012 | Shelton, IV et al. | |
| 2013/0126581 | A1 | 5/2013 | Yates et al. | |
| 2015/0157321 | A1 | 6/2015 | Zergiebel et al. | |
| 2015/0235789 | A1 | 8/2015 | Calderoni | |
| 2016/0030040 | A1 | 2/2016 | Calderoni et al. | |

* cited by examiner 100
102
110a
110b
112
114
108
180b
92
82
165
160
90
80
150
124
134b
134a
134
127
136
126
126a
130
20
22
10
128
125
5
14
12
124a

VARIABLE SPEED CONTROL OF POWERED SURGICAL DEVICE

BACKGROUND

1. Technical Field

The present disclosure relates to surgical devices and, more specifically, to speed control systems for powered surgical devices.

2. Discussion of Related Art

A number of surgical device manufacturers have developed product lines with proprietary drive systems for operating or manipulating the surgical device. In many instances the surgical devices include a handle assembly, which is reusable, and a disposable end effector or the like that is selectively connected to the handle assembly prior to use and then disconnected from the handle assembly following use in order to be disposed of or in some instances sterilized for re-use.

Many of the existing end effectors for use with many of the existing surgical devices or handle assemblies linearly advance a firing assembly to actuate the end effector. For example, end effectors for performing endo-gastrointestinal anastomosis procedures, end-to-end anastomosis procedures, and transverse anastomosis procedures, each typically require a linear advancement of a firing assembly in order to be operated.

Existing handle assemblies advance the firing assemblies at a predetermined speed. In addition, some handle assemblies include feedback systems that reduce the predetermined speed in response to surgical conditions such as tissue thickness. However, a clinician using the surgical device lacks control of the firing speed of the handle assembly.

Accordingly, there is a need to provide a clinician with an ability to vary the speed of advancement a firing assembly based surgical conditions observed by the clinician.

SUMMARY

In an aspect of the present disclosure, a surgical device includes a housing, a drive shaft, a motor, a control button, and a motor speed controller. The motor is configured to rotate the drive shaft that is disposed within housing. The control button is disposed on the housing and the motor speed controller is operably associated with the control button. The motor speed controller varies an angular velocity of the motor as a function of a percent of actuation of the control button between an unactuated position and a fully actuated position.

In aspects, the motor speed controller includes a magnet and a Hall Effect sensor. The magnet may be attached to the control button and the Hall Effect sensor may be fixedly mounted within the housing.

In some aspects, the motor speed controller includes a light source, a set of louvers, and a photo sensor. The set of louvers may be disposed between the light source and the photo sensor. The set of louvers can have a closed configuration in which the set of louvers prevent light emitted from the light source from reaching the photo sensor and an open configuration in which at least a portion of light emitted from the light source illuminates the photo sensor. The motor speed controller may include a drive gear operably associated with the set of louvers to transition the set of louvers between the open and closed configurations. The control button may include a rod having a toothed rack that meshingly engages the drive gear to transition the set of louvers between the open and closed configurations in response to actuation of the control button.

The function can be a linear function or a stepped function. When the function is a stepped function, the stepped function can be a two or a three step function. The stepped function can have a dead spot between about zero percent and about five percent actuation of the control button where the motor does not rotate the drive shaft.

In certain aspects, the surgical device includes a biasing member disposed about the control button to urge the control button towards the unactuated position. The biasing member can have a spring constant such that an actuation force required to actuate the control button linearly increases to affect actuation of the control button towards the fully actuated position. Alternatively, the biasing member can have a first spring constant and a second spring constant such that an actuation force required to actuate the control button increases in a stepped manner to affect actuation of the control button towards the fully actuated position.

In another aspect of the present disclosure, a method of controlling an angular velocity of a drive shaft of a motor of a surgical device includes actuating a control button of the surgical device a first distance towards a fully actuated position such that a motor speed controller transmits a control signal to the motor to rotate the drive shaft at a first angular velocity and continuing to actuate the control button of the surgical device a second distance towards the fully actuated position such that the motor speed controller transmits a second control signal to the motor to rotate the drive shaft a second angular velocity greater than the first angular velocity.

In aspects, continuing to actuate the control button of the surgical device a section distance transitions a set of louvers towards an open configuration such that an amount of light emitted from a light source reaching a photo sensor increases. Alternatively, continuing to actuate the control button of the surgical device a second distance can move a magnet closer to a Hall Effect sensor.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
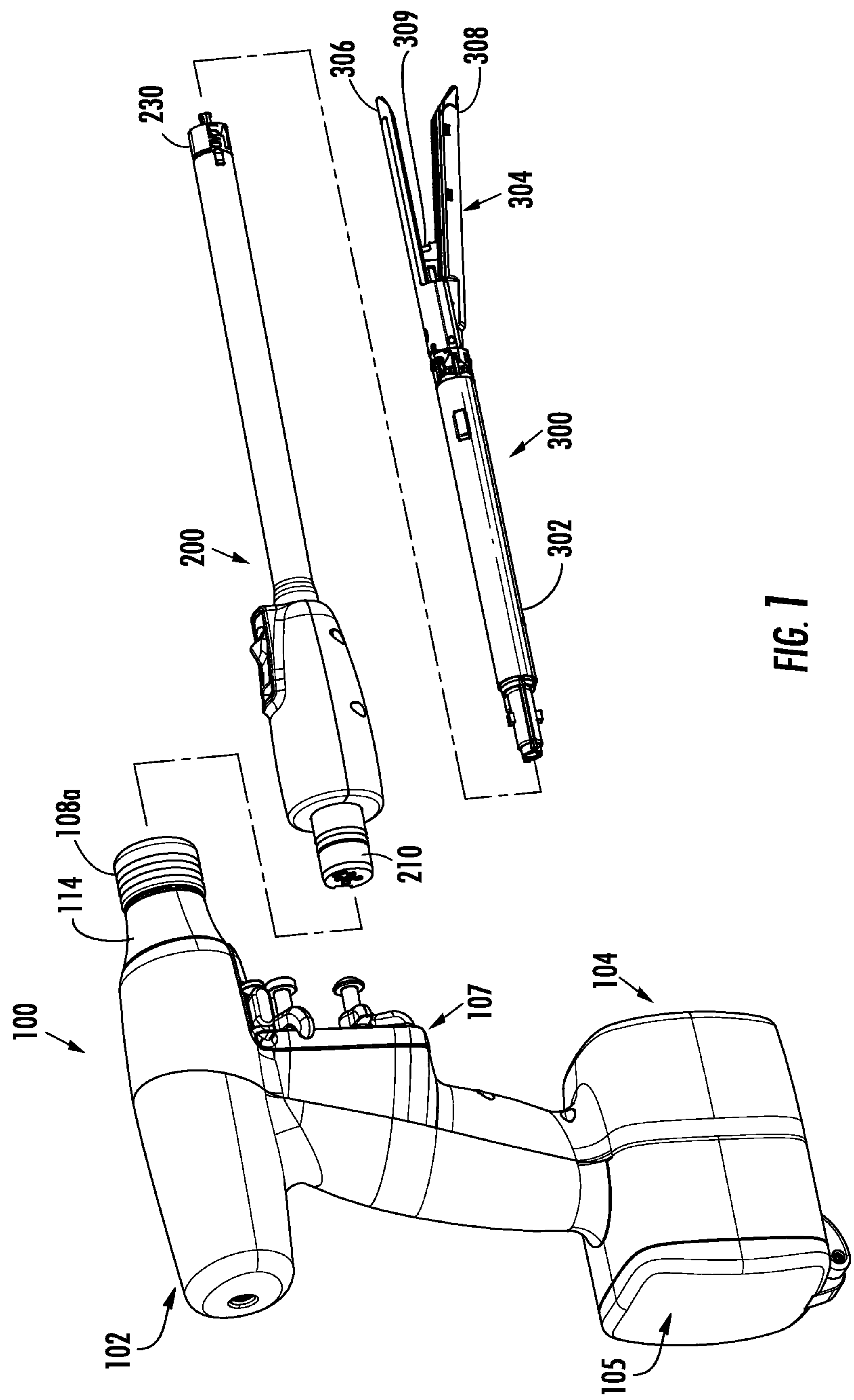
FIG. 1 is a perspective view, with parts separated, of a surgical device and adapter, in accordance with an embodiment of the present disclosure, illustrating a connection thereof with an end effector.

This disclosure relates generally to variable speed controls for powered surgical devices. The powered surgical devices include motor speed controls for varying the speed of motors of the powered surgical device. As detailed below, the motor speed controls may include a magnet disposed on a control button and a Hall Effect sensor positioned on a control board adjacent the control button. As the control button is actuated, the Hall Effect sensor detects the magnetic field generated by the magnet to determine the actuation of the motor speed control. Alternatively, the motor speed control may include a control button, a light source, a set of louvers, and a photo sensor. The control button is operably coupled to the set of louvers which are disposed between the light source and the photo sensor and function to vary an amount of light, emitted from the light source, that is received by the photo sensor in response to actuation of the control button.

Embodiments of the present disclosure are now described in detail with reference to the drawings in which like reference numerals designate identical or corresponding elements in each of the several views. As used herein, the term “clinician” refers to a doctor, a nurse, or any other care provider and may include support personnel. Throughout this description, the term “proximal” refers to the portion of the device or component thereof that is closest to the clinician and the term “distal” refers to the portion of the device or component thereof that is farthest from the clinician.

A surgical device, in accordance with an embodiment of the present disclosure, is generally designated as 100, and is in the form of a powered hand held electromechanical device configured for selective attachment thereto of a plurality of different end effectors that are each configured for actuation and manipulation by the powered hand held electromechanical surgical device.

As illustrated in FIG. 1, the surgical device 100 is configured for selective connection with an adapter 200, and, in turn, adapter 200 is configured for selective connection with an end effector or single use loading unit 300. As detailed herein, end effector 300 is a stapling end effector; however, it is contemplated that the surgical device 100 may be selectively connected to a plurality of end effectors that are configured to perform a variety of surgical procedures to tissue (e.g., stapling, sealing, dissecting, and sampling).

Figure 2:
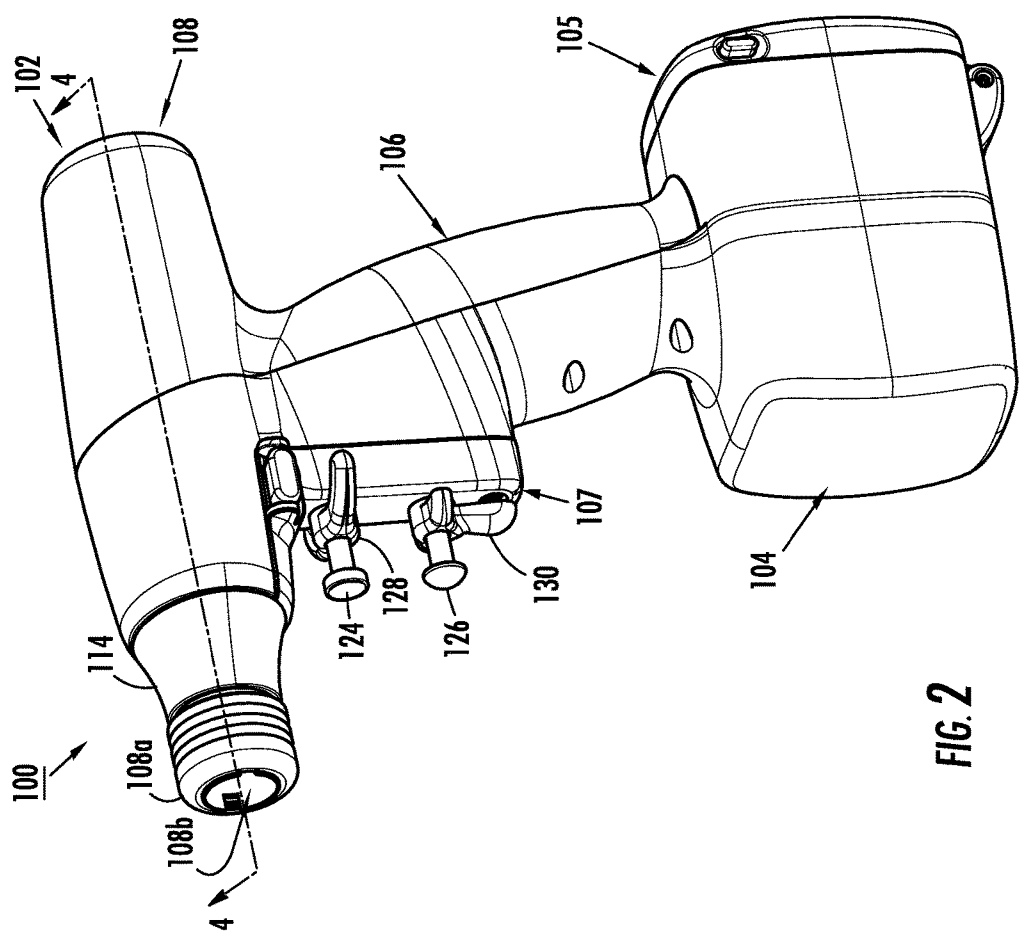
FIG. 2 is a perspective view of the surgical device of FIG. 1.
Figure 3:
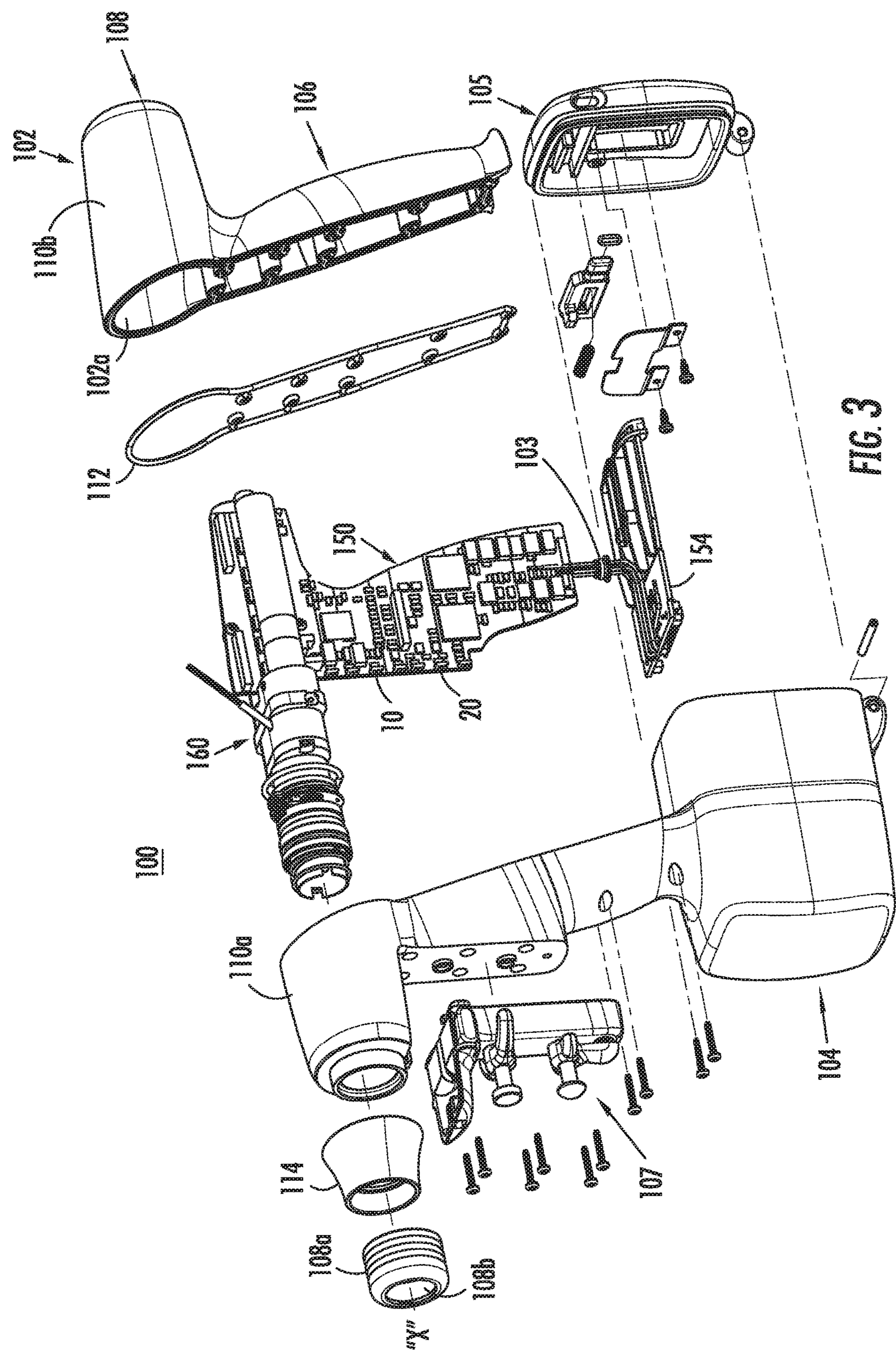
FIG. 3 is a perspective view, with parts separated, of the surgical device of FIGS. 1 and 2.

As illustrated in FIGS. 1-3, the surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110*a* that is integrally formed with and extending from the lower portion 104, and a proximal half-section 110*b* connectable to distal half-section 110*a* by a plurality of fasteners. When joined, distal and proximal half-sections 110*a*, 110*b* define a handle housing 102 having a cavity 102*a* therein in which a circuit board 150 and a drive mechanism 160 is situated.

Upper housing portion 108 of handle housing 102 provides a housing in which drive mechanism 160 is situated. The drive mechanism 160 is configured to drive shafts and/or gear components in order to perform the various operations of the surgical device 100. In particular, drive mechanism 160 is configured to drive shafts and/or gear components in order to selectively move tool assembly 304 of end effector 300 (FIG. 1) relative to proximal body portion 302 of end effector 300, to rotate end effector 300 about a longitudinal axis “X” (FIG. 3) relative to handle housing 102, to move anvil assembly 306 relative to cartridge assembly 308 of end effector 300 between open and clamped positions, or to fire a stapling and cutting cartridge within cartridge assembly 308 of end effector 300 to eject staples (not explicitly shown) from the cartridge assembly 308 and to advance a knife 309 through the cartridge assembly 308.

The drive assembly 160 includes a first motor 80 that rotates a first drive shaft 82 and a second motor 90 that rotates a second drive shaft 92. The first drive shaft 82 is operatively associated with the end effector 300 such that rotation of the first drive shaft 82 fires stapling and cutting cartridge within the cartridge assembly 308. The second drive shaft 92 is operatively associated with the end effector 200 such that rotation of the second drive shaft rotates the end effector 200 about the longitudinal axis “X” as detailed below. It is contemplated that the first and second drive shafts 82, 92 may be operatively associated with different functions of the end effector 200. Such functions can include articulation of the end effector, clamping tissue, firing staples and/or cutting tissue, etc.

Exemplary examples of electromechanical, hand-held, powered surgical devices and adapters are disclosed in commonly owned U.S. Pat. Nos. 8,968,276 and 9,055,943, commonly owned U.S. Patent Publication No. 2015/0157321, and commonly owned U.S. Provisional Patent Application Ser. No. 62/291,775, filed Feb. 5, 2016, entitled “HANDHELD ELECTROMECHANICAL SURGICAL SYSTEM,” the entire contents of each of these disclosures are hereby incorporated by reference.

As illustrated in FIGS. 1-3, the handle housing 102 supports a trigger housing 107 on a distal surface or side of the intermediate housing portion 108. The trigger housing 107, in cooperation with the intermediate housing portion 108, supports a pair of finger-actuated control buttons 124, 126 and rocker devices 128, 130. In particular, the trigger housing 107 defines an upper aperture 125 for slidably receiving a first control button 124, and a lower aperture 127 for slidably receiving a second control button 126. Each one of the control buttons 124, 126 is moved or actuated by a clinician to affect movement of the end effector 300.

The trigger housing 107 includes biasing members 134, 136 operably associated with the control buttons 124, 126, respectively. Each of the biasing members 134, 136 is disposed about a respective control button 124, 126 to bias the respective control button 124, 126 towards the unactuated position. The biasing members 134, 136 resist actuation of the control buttons 124, 126, respectively, such that an actuation force is required to move each of the control buttons 124, 126 towards the fully actuated position. The biasing members 134, 136 can have a linear spring constant such that the actuation force linearly increases as the respective control button 124, 126 is actuated. Alternatively, the biasing member 134 can include a first spring 134*a* and a second spring 134*b* such that the actuation force increases in a stepped manner as the control button 124 is actuated. Specifically, in a first step of actuation of the control button 124, the first spring 134*a* is compressed and in a second step of actuation of the control button 124, the first and second springs 134*a*, 134*b* are compressed. It is contemplated that the second biasing member 136 can also require a stepped actuation force to actuate the control button 126. It is envisioned that the first and/or second biasing members 134, 136 can be constructed of a single spring having a spring rate that varies as the spring is compressed such that the actuation force increases in a stepped manner or in an exponential manner as the control button 124, 126 is actuated.

Figures 4, 5:
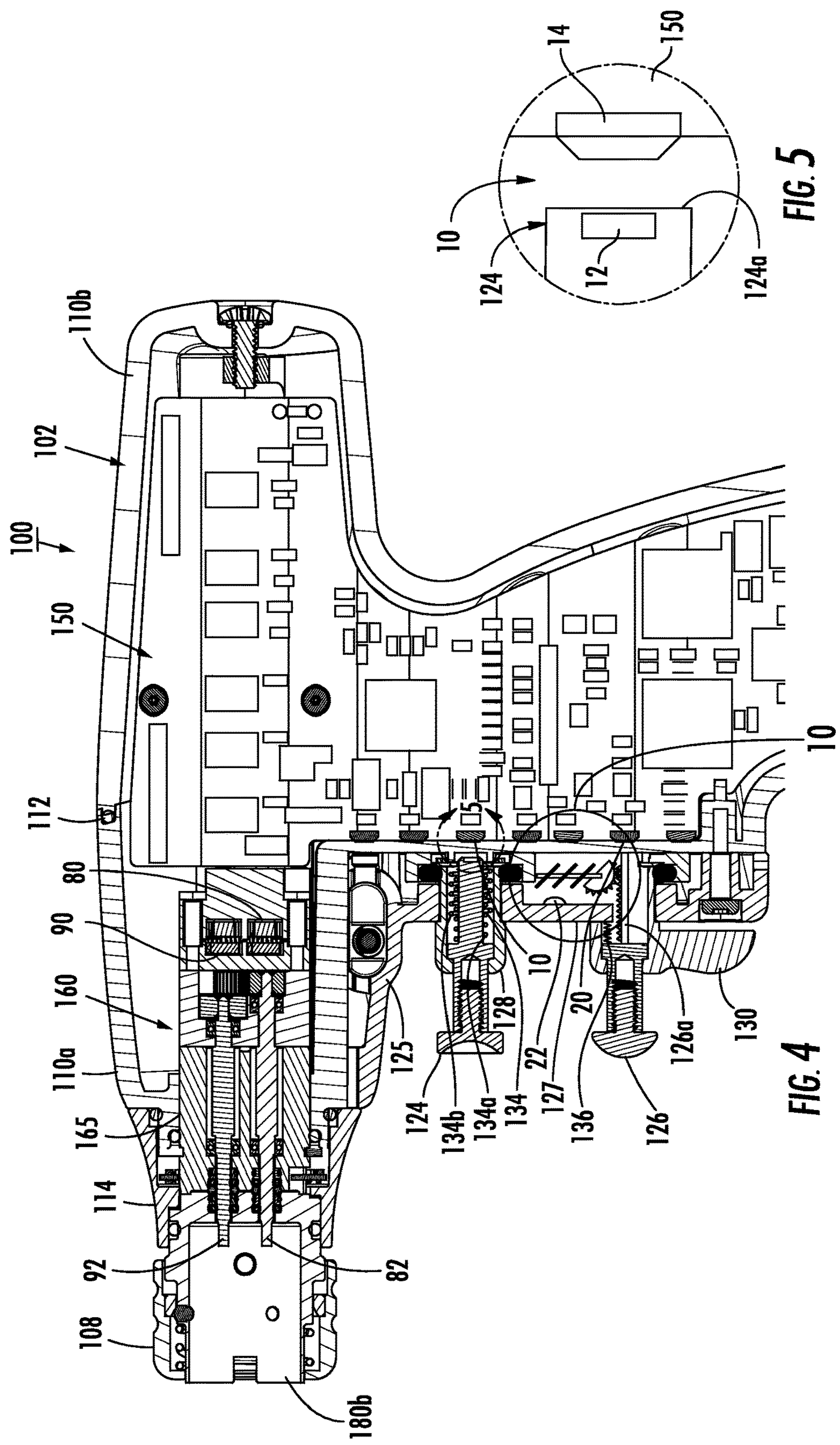
FIG. 4 is a cross-sectional view taken along the section line 4-4 of FIG. 2.
FIG. 5 is an enlarged view of the area of detail of FIG. 4.

With reference to FIG. 4, the circuit board 150 includes first and second motor speed controls 10, 20 that are engaged by the control buttons 124, 126 to affect movement of the end effector 300. Each of the first and second motor speed controls 10, 20 are in communication with the drive assembly 160 to affect rotation of the first and second drive shafts 82, 92, respectively. Specifically, the first motor speed control 10 is in communication with the motor 80 to control the rotational speed of first drive shaft 82 and the second motor speed control 20 is in communication with the motor 90 to control the rotational speed of the second drive shaft 92.

Referring also to FIG. 5, the first motor speed control 10 includes a magnet 12 and a Hall Effect sensor 14. The magnet 12 is mounted to the control button 124 and is moveable towards and away from the Hall Effect sensor 14. The Hall Effect sensor 14 is mounted to the circuit board 150 to determine a distance or gap to the magnet 12. From the distance between the Hall Effect sensor 14 to the magnet 12, the first motor speed control 10 determines an extent that the control button 124 is depressed. The first motor speed control sends a control signal to the motor 80 indicative of the position of the control button 124 to affect rotation of the first drive shaft 82, as described in greater detail below.

Figure 6:
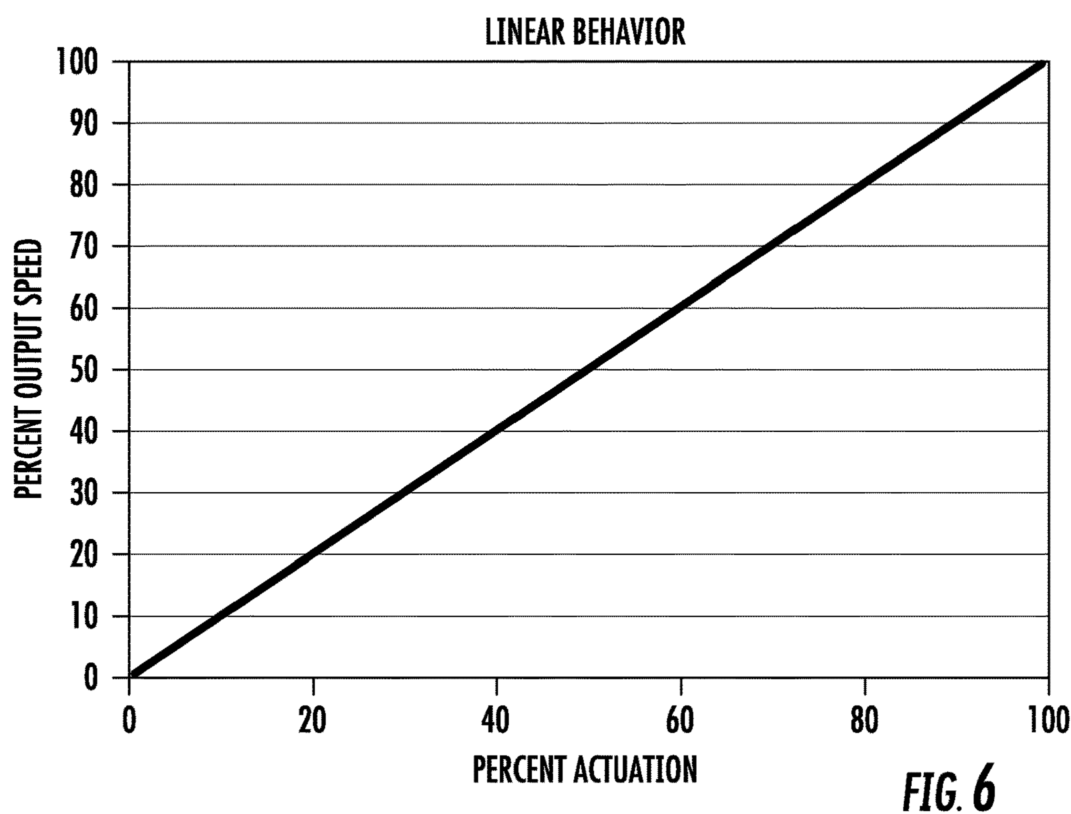
FIG. 6 is a graph depicting output speed of a motor of the surgical device of FIG. 1 as a linear function of actuation of a control button of the surgical device of FIG. 1.

With additional reference to FIGS. 6-9, the control signal controls an output speed (i.e., angular velocity of rotation) of the motor 80 as a function of actuation of the control button 124. The actuation of the control button 124 is measured from an unactuated or nondepressed position as 0% actuation and a fully depressed position as 100% actuation. With particular reference to FIG. 6, the output speed of the motor 80 is a linear function of the percent of actuation of the control button 124. Specifically, the motor 80 rotates a percent of its maximum output speed that correlates to a percent of actuation of the control button 124.

Figure 7:
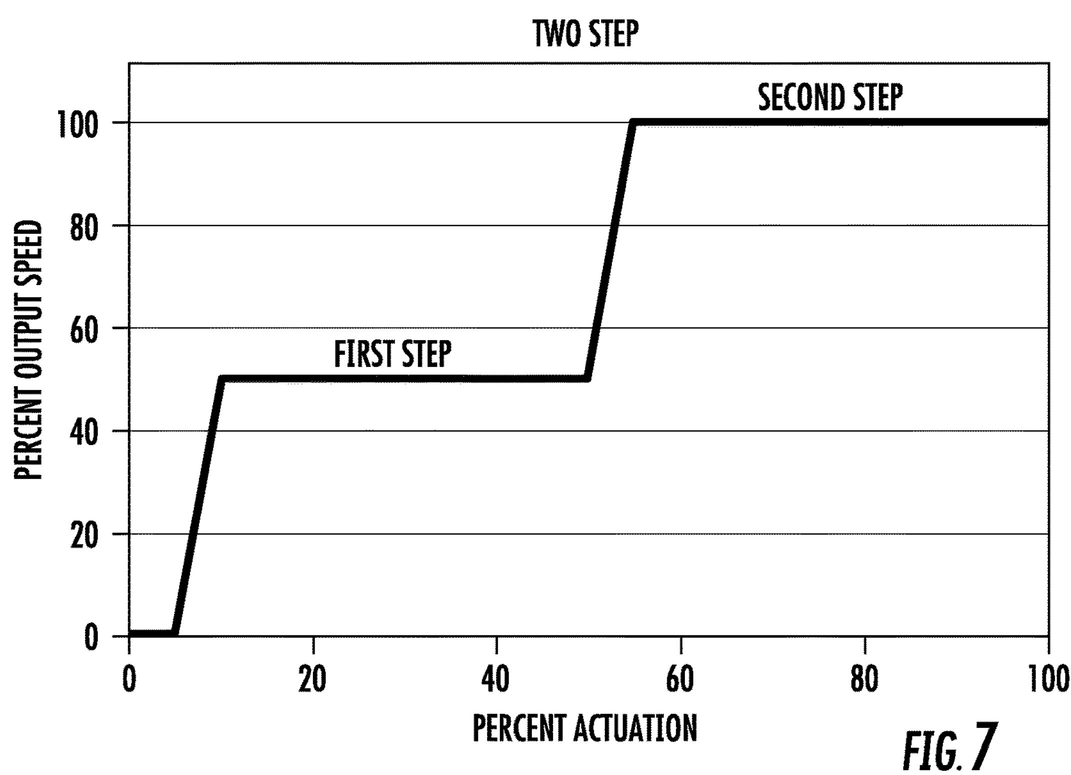
FIG. 7 is a graph depicting output speed of a motor of the surgical device of FIG. 1 as a two-step function of actuation of a control button of the surgical device of FIG. 1.
Figure 8:
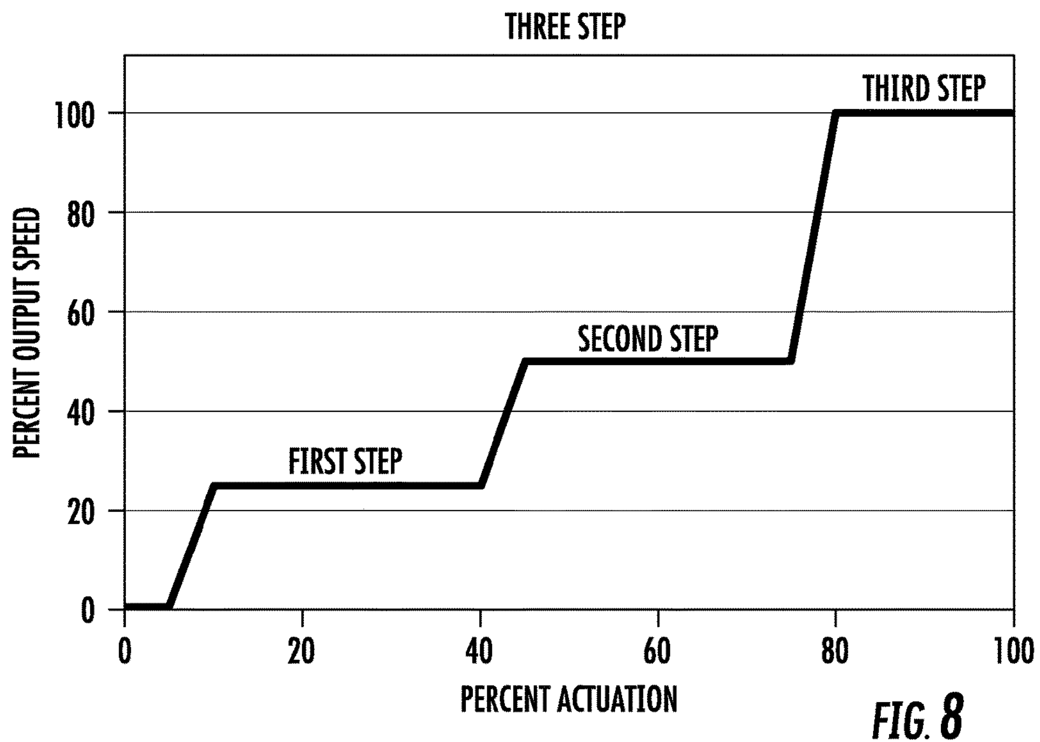
FIG. 8 is a graph depicting output speed of a motor of the surgical device of FIG. 1 as a three-step function of actuation of a control button of the surgical device of FIG. 1.
Figure 9:
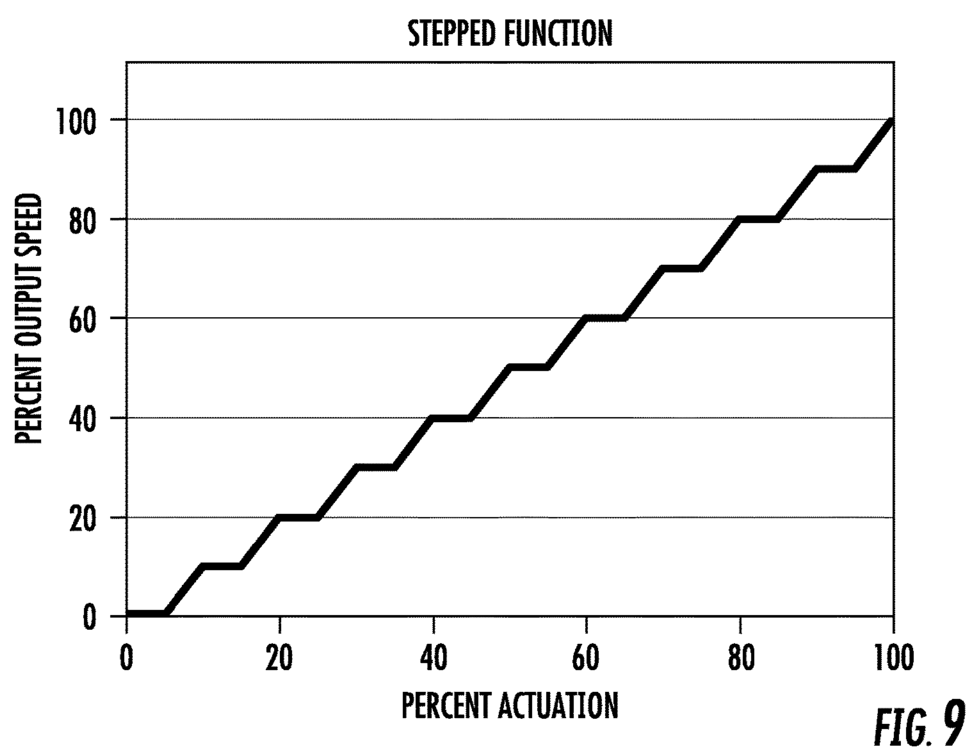
FIG. 9 is a graph depicting output speed of a motor of the surgical device of FIG. 1 as a stepped function of actuation of a control button of the surgical device of FIG. 1.

Alternatively, as shown in FIGS. 7-9, the output speed of the motor 80 is a step function of the percent of actuation of the control button 124. With reference to FIG. 7, the output speed of the motor 80 is a two-step function of the percent of actuation of the control button 124. Specifically, the control button 124 has a dead zone between 0% and about 5% of actuation where the motor 80 does not rotate, a first step between about 5% and about 50% of actuation of the control button 124 where the motor 80 rotates at a low speed of about 50% of its maximum output speed, and a second step between about 50% and 100% of actuation of the control button 124 where the motor 80 rotates at a high speed at its maximum output speed.

With reference to FIG. 8, the output speed of the motor 80 is a three step function of the percent of actuation of the control button 124. Specifically, the control button 124 has a dead zone between 0% and about 5% of actuation where the motor 80 does not rotate, a first step between about 5% and about 40% of actuation of the control button 124 where the motor 80 rotates at a low speed of about 25% of its maximum output speed, a second step between about 40% and about 75% of actuation of the control button 124 where the motor 80 rotates at a mid-speed of about 50% of its maximum output speed, and a third step between about 75% and 100% of actuation of the control button 124 where the motor 80 rotates at a high speed at its maximum output speed. Other ranges and percentages are contemplated within the scope of the present disclosure.

With reference to FIG. 9, the output speed of the motor 80 can be a stepped function with a plurality of steps that increase the output speed of the motor 80 in response to the percent of actuation of the control button 124.

Table 1 below shows the output speed percent of the motor 80 as a percent of actuation of the control button 124 for each of the functions detailed above.

TABLE 1

| Percent of Actuation | Linear Function | Two-Step Function | Three-Step Function | Stepped Function |
|---|---|---|---|---|
| 0 | 0 | 0 | 0 | 0 |
| 5 | 5 | 0 | 0 | 0 |
| 10 | 10 | 50 | 25 | 10 |
| 15 | 15 | 50 | 25 | 10 |
| 20 | 20 | 50 | 25 | 20 |
| 25 | 25 | 50 | 25 | 20 |
| 30 | 30 | 50 | 25 | 30 |
| 35 | 35 | 50 | 25 | 30 |
| 40 | 40 | 50 | 25 | 40 |
| 45 | 45 | 50 | 50 | 40 |
| 50 | 50 | 50 | 50 | 50 |
| 55 | 55 | 100 | 50 | 50 |
| 60 | 60 | 100 | 50 | 60 |
| 65 | 65 | 100 | 50 | 60 |
| 70 | 70 | 100 | 50 | 70 |
| 75 | 75 | 100 | 50 | 70 |
| 80 | 80 | 100 | 100 | 80 |
| 85 | 85 | 100 | 100 | 80 |
| 90 | 90 | 100 | 100 | 90 |
| 95 | 95 | 100 | 100 | 90 |
| 100 | 100 | 100 | 100 | 100 |
| | Output Speed Percent | | | |

Figure 11:
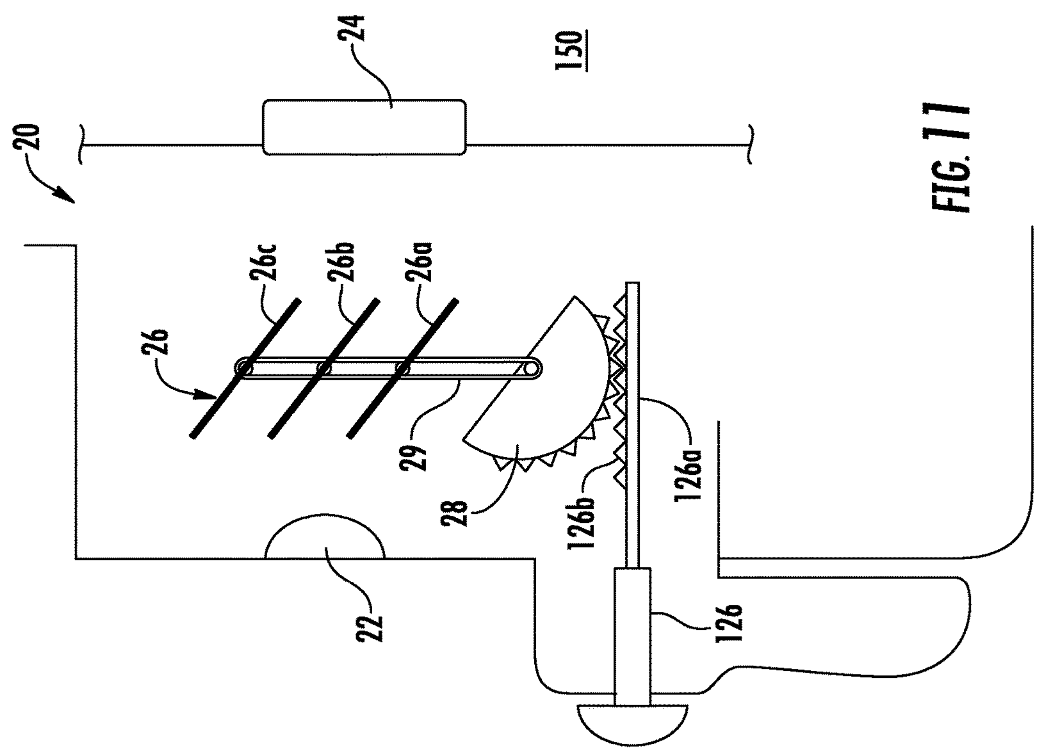
FIG. 11 is a view similar to the view of FIG. 10 showing the set of louvers in an open configuration.
Figure 10:
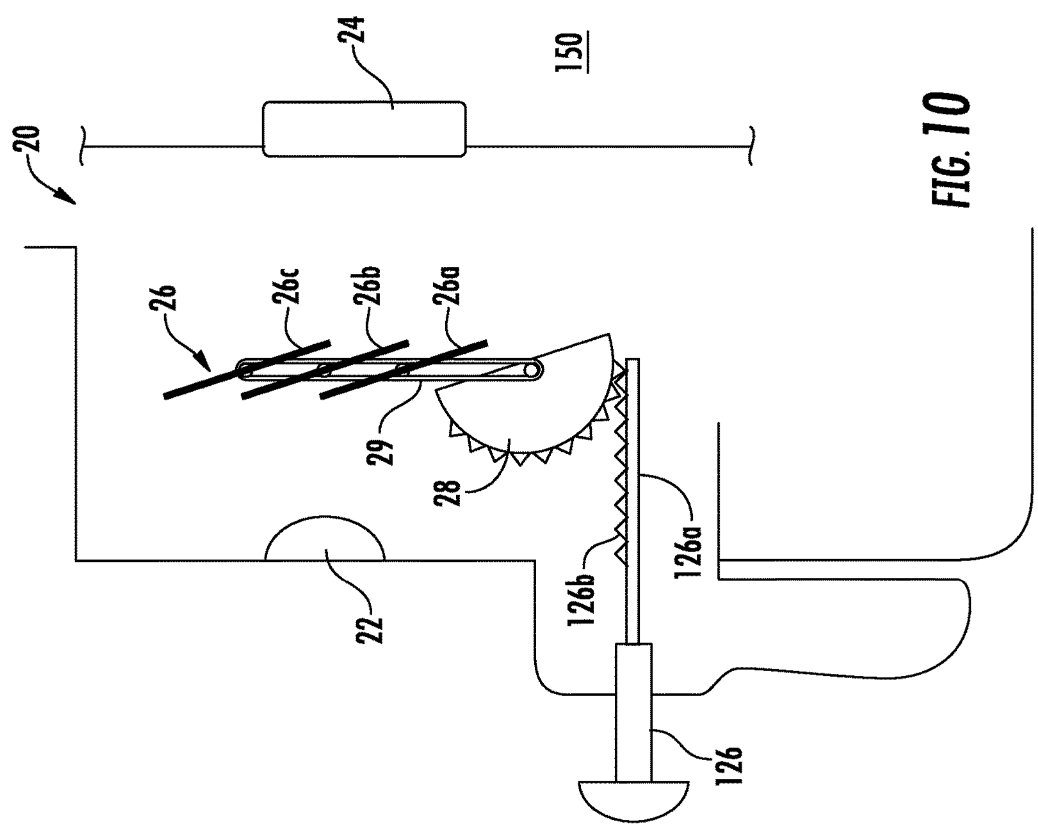
FIG. 10 is an enlarged view of the area of detail of FIG. 4 showing a set of louvers in a closed configuration.

With reference to FIGS. 4, 10, and 11, the second motor speed control 20 includes a light source 22, a photo sensor 24, a set of louvers 26, and a drive gear 28. The light source 22 is disposed within the lower aperture 127 of the trigger housing 107 and the photo sensor 24 is mounted to the control board 150 and positioned to receive light emitted from the light source 22. The set of louvers 26 is positioned between the light source 22 and the photo sensor 24. The set of louvers 26 has a closed or substantially closed configuration (FIG. 10) in which the set of louvers 26 prevents or limits light, emitted from the light source 22, from reaching the photo sensor 24, and an open or substantially open configuration (FIG. 11) in which the set of louvers 26 allows at least a portion or a majority of light, emitted from the light source 22, to reach the photo sensor 24.

The set of louvers 26 includes a first louver 26*a*, a second louver 26*b*, and a third louver 26*c* that are operably coupled to a drive belt 29 extending from the drive gear 28. The control button 126 includes a rod 126*a* extending towards the circuit board 150. The rod 126*a* includes a toothed rack 126*b* that is meshingly engaged with teeth 28*a* of the drive gear 28. As the control button 126 is actuated from an unactuated position (FIG. 10) towards an actuated position (FIG. 11), the toothed rack 126*b* rotates the drive gear 28 which pivots the set of louvers 26 from the closed configuration towards the open configuration. As the set of louvers 26 pivots towards the open configuration, an amount of light emitted from the light source 22 and received by the photo sensor 24 increases. As shown, the set of louvers 26 includes three louvers 26*a-c*; however, it is contemplated that the set of louvers 26 can include 1, 2, or more than three louvers.

In response to receiving light emitted from the light source 22, the photo sensor 24 sends a control signal to the motor 90 to affect rotation of the second drive shaft 92. The control signal controls an output speed (i.e., angular velocity of rotation) of the motor 90 as a function of the amount of light received by the photo sensor 24 and thus, actuation of the control button 126. The actuation of the control button 126 is measured from an unactuated or nondepressed position as 0% actuation and a fully depressed position as 100% actuation. With particular reference to FIG. 6, the output speed of the motor 90 is a linear function of the percent of actuation of the control button 126. Specifically, the motor 90 rotates a percent of its maximum output speed that correlates to a percent of actuation of the control button 126.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical device comprising:

a housing;

a drive shaft;

a motor for rotating the drive shaft disposed within the housing;

a control button disposed on the housing; and a motor speed controller operably associated with the control button, the motor speed controller varying an angular velocity of the motor as a function of a percent of actuation of the control button between an unactuated position and a fully actuated position, the motor speed controller including a light source, a set of louvers, and a photo sensor.

2. The surgical device according to claim 1, wherein the set of louvers is disposed between the light source and the photo sensor, the set of louvers having a closed configuration in which the set of louvers prevent light emitted from the light source from reaching the photo sensor and an open configuration in which at least a portion of light emitted from the light source illuminates the photo sensor.

3. The surgical device according to claim 2, wherein the motor speed controller includes a drive gear operably associated with the set of louvers to transition the set of louvers between the open and closed configurations.

4. The surgical device according to claim 3, wherein the control button includes a rod having a toothed rack that meshingly engages the drive gear to transition the set of louvers between the open and closed configurations in response to actuation of the control button.

5. The surgical device according to claim 1, wherein the function is a linear function or a stepped function.

6. The surgical device according to claim 5, wherein the stepped function is a two-step function.

7. The surgical device according to claim 5, wherein the stepped function is a three-step function.

8. The surgical device according to claim 5, wherein the stepped function has a dead spot between about 0% and about 5% of actuation of the control button where the motor does not rotate the drive shaft.

9. The surgical device according to claim 1, further comprising a biasing member disposed about the control button to urge the control button towards the unactuated position.

10. The surgical device according to claim 9, wherein the biasing member has a spring constant such that an actuation force required to actuate the control button linearly increases to affect actuation of the control button towards the fully actuated position.

11. The surgical device according to claim 9, wherein the biasing member has a first spring constant and a second spring constant such that an actuation force required to actuate the control button increases in a stepped manner to affect actuation of the control button towards the fully actuated position.

12. A method of controlling an angular velocity of a driveshaft of a motor of a surgical device, the method comprising:

actuating a control button of the surgical device a first distance towards a fully actuated position such that a motor speed controller transmits a control signal to the motor to rotate the drive shaft at a first angular velocity; and continuing to actuate the control button of the surgical device a second distance towards the fully actuated position to transition a set of louvers towards an open configuration such that an amount of light emitted form a light source reaching a photo sensor increases such that the motor speed controller transmits a second control signal to the motor to rotate the drive shaft a second angular velocity greater than the first angular velocity.

* * * * *